US006398711B1

(12) United States Patent
Green et al.

(10) Patent No.: US 6,398,711 B1
(45) Date of Patent: Jun. 4, 2002

(54) PIVOTING NEEDLE TEMPLATE APPARATUS FOR BRACHYTHERAPY TREATMENT OF PROSTATE DISEASE AND METHODS OF USE

(75) Inventors: Thomas C. Green, SW. Seattle, WA (US); Michael J. Horzewski, San Jose, CA (US)

(73) Assignee: Neoseed Technology LLC, San Francisco, CA (US)

( * ) Notice: Subject to any disclaimer, the term of this patent is extended or adjusted under 35 U.S.C. 154(b) by 0 days.

(21) Appl. No.: 09/648,091

(22) Filed: Aug. 25, 2000

(51) Int. Cl.[7] ............................. A61M 36/00; A61N 5/00
(52) U.S. Cl. ................................................ 600/7; 606/130
(58) Field of Search ........................... 600/1–8; 606/130

(56) References Cited

U.S. PATENT DOCUMENTS

| | | |
|---|---|---|
| 4,167,179 A | 9/1979 | Kirch |
| 5,242,373 A * | 9/1993 | Scott et al. ................. 600/7 |
| 5,626,829 A | 5/1997 | Koutrouvelis |
| 5,871,448 A | 2/1999 | Ellard |
| 5,928,130 A | 7/1999 | Schmidt |
| 5,938,583 A | 8/1999 | Grimm |
| 5,957,935 A | 9/1999 | Brown et al. |
| 6,036,632 A * | 3/2000 | Whitmore, III et al. ........ 600/7 |
| 6,311,084 B1 * | 10/2001 | Cormack et al. .............. 600/7 |

* cited by examiner

Primary Examiner—John P. Lacyk
(74) Attorney, Agent, or Firm—Fish & Neave; Nicola A. Pisano

(57) ABSTRACT

Methods and apparatus are provided for improved brachytherapy treatment of prostate disease. The apparatus comprises a needle template mount for use with standard brachytherapy apparatus. The mount provides for angular reorientation of a needle template with respect to an ultrasound probe during brachytherapy administration. Angular reorientation is expected to beneficially overcome anatomical constraints, such as skeletal structures, that may limit a medical practitioner's ability to deliver radioactive brachytherapy seeds into a prostate in proper alignment. The mount comprises an arc slot in which the template may translate to achieve angular reorientation. A guide tube is also provided to ensure straight advancement of brachytherapy needles.

42 Claims, 4 Drawing Sheets

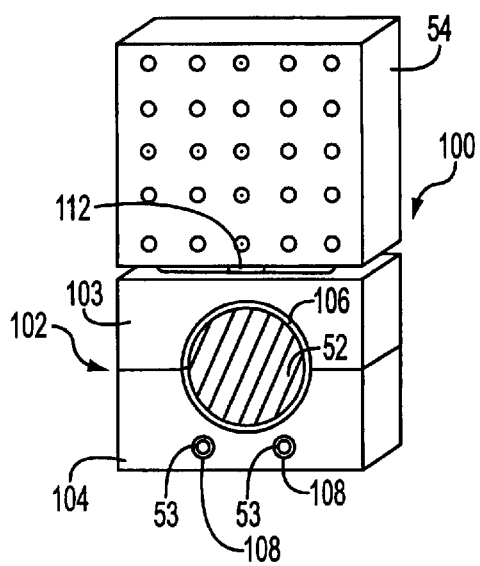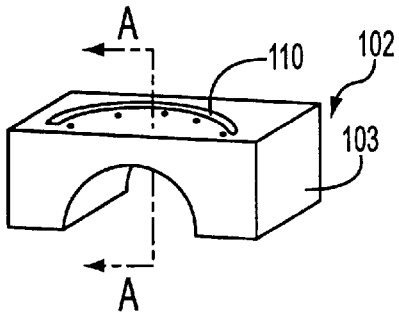
FIG. 3A             FIG. 3B
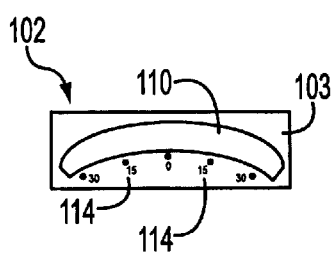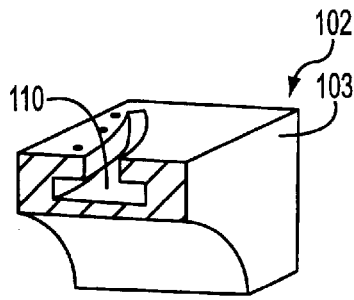
FIG. 3C             FIG. 3D
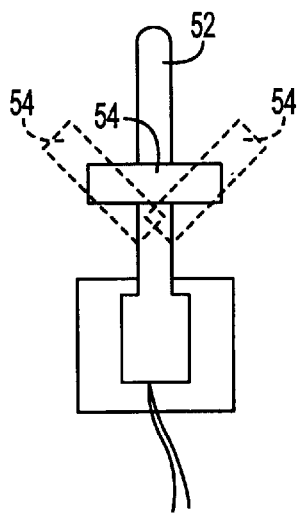
FIG. 3E

PIVOTING NEEDLE TEMPLATE APPARATUS FOR BRACHYTHERAPY TREATMENT OF PROSTATE DISEASE AND METHODS OF USE

FIELD OF THE INVENTION

This invention relates to improved apparatus and methods for the treatment of prostate cancer. More particularly, the present invention provides a needle template mount that provides for angular reorientation of a needle template for more effective administration of brachytherapy.

BACKGROUND OF THE INVENTION

Excluding nonmelanoma skin cancers, prostate cancer is the most common cancer afflicting American men. The American Cancer Society estimates that over 180,00 new cases will be diagnosed in the U.S. in the year 2000 alone, and that nearly 32,000 people will die from the disease. Prostate cancer is second only to lung cancer as the leading cause of cancer death in men, accounting for roughly 11%.

Prostate cancer is defined as malignant tumor growth within the prostate gland. Its cause is unknown, although high dietary fat intake and increased testosterone levels are believed to be contributory factors. A letter scale ("A" through "D"), which accounts for aggressiveness and differentiation, is commonly used to classify the stage of disease. In Stage A, the tumor is not palpable but is detectable in microscopic biopsy. Stage B is characterized by a palpable tumor confined to the prostate. By Stage C, the tumor extends beyond the prostate with no distant metastasis. By Stage D, cancer has spread to the regional lymph nodes.

In the early stages, prostate cancer is most commonly treated by prostate removal or by brachytherapy. More advanced cases are treated by hormonal manipulation or orchiectomy to reduce testosterone levels and curb spreading of the disease, by chemotherapy, or by external beam radiation therapy.

With regard to treatment of early stage prostate cancer, the state of the art has several drawbacks. Radical prostatectomy is often recommended for treatment of localized stage A and B prostate cancers. Under general or spinal anesthesia, an incision is made through a patient's abdomen or perineal area, and the diseased prostate is removed. The procedure is lengthy, especially if a lymph node dissection is simultaneously performed, and requires a hospital stay of 7–10 days. Possible complications include impotence and urinary incontinence.

Internal radiation therapy or brachytherapy has recently been developed and holds great promise for the treatment of early stage prostate cancer. Radioactive pellets or seeds of, for example, iodine-125, palladium-103, or iridium-192, are deposited directly and permanently into the prostate through a small incision. Imaging techniques, such as transrectal ultrasound, CT scans, or MRI, are used to accurately guide placement of the radioactive material. Advantageously, radiation from the brachytherapy seeds is administered directly to the prostate with less damage to surrounding tissues, delivering a substantially higher radiation dosage to the prostate than to the surrounding tissues, as compared to external beam radiation therapy. The procedure need only be performed once, and impotence and urinary incontinence complications are significantly reduced, as compared to prostate removal procedures.

The radioactive seeds are placed inside thin needles, which are inserted through the skin of the perineum (area between the scrotum and anus) into the prostate. U.S. Pat. No. 5,928,130 Schmidt provides a slightly modified example of such a needle device. Each needle is slowly retracted with a spinning motion by a first practitioner while a plunger within the needle, and proximal of the radioactive seeds, is held stationary by a second practitioner. The plunger keeps the seeds in place during retraction of the needle, while rotation of the needle during retraction delivers the seeds in a line within the prostate.

The seeds, which are permanently implanted, give off radiation for weeks or months. Their presence causes little discomfort, and they remain in the prostate after decay of the radioactivity. For several weeks following needle insertion, patients may experience pain in the perineal area, and urine may have a red-brown discoloration.

Although, when performed correctly, radioactive seed implantation may provide several benefits as compared to prostate removal and other techniques, current surgical apparatuses and methods for delivering the seeds to target locations within the prostate are somewhat crude and are subject to practitioner error. U.S. Pat. No. 5,871,448 Ellard, for example, describes apparatus similar to that currently in widespread use. The apparatus includes a needle template with a template holder. The template may be moved longitudinally along a track to alter the distance between the template and a patient's perineum. The template holder is then rigidly affixed to the track, and brachytherapy needles are passed through the needle template to stabilize the needles prior to insertion through the patient's perineum. A drawback of the Ellard device is that, apart from longitudinal adjustment, a medical practitioner is not able to alter the orientation of the template.

U.S. Pat. No. 5,957,935 Brown et al. describes a disposable needle template that need not be painstakingly sterilized. It further discloses a mount for the template that may be oriented in multiple planes. Specifically, the template may be positioned longitudinally, horizontally, and vertically. Although Brown's apparatus may provide improved needle template orientation capabilities as compared to Ellard's apparatus, it permits constrained movement, and does not allow simultaneous reorientation in multiple planes, as is necessary to change the angle of attack between the template and the patient.

A preferred angular orientation of the needle template may vary from needle to needle during a procedure due to anatomical constraints, including skeletal structures. Thus, a template that allows only one angular orientation is not optimal and may lead to incorrect placement of radioactive seeds within a patient's prostate.

U.S. Pat. No. 5,626,829 Koutrouvelis provides a stereotactic assembly for orienting a template vertically, horizontally, rotatably, and angularly. While the assembly may be effective for the transgluteal brachytherapy procedure described by Koutrouvelis, it is not tailored for the more commonly used transperineal approach. For example, it does not provide for longitudinal adjustment of the needle template. Furthermore, the assembly is large and may prove cumbersome in the smaller surgical field of transperineal procedures.

In view of the drawbacks associated with orienting previously-known needle templates, it would be desirable to provide methods and apparatus that overcome such drawbacks.

It further would be desirable to provide methods and apparatus with improved orientation capabilities, sized to permit use in the surgical field of standard, transperineal brachytherapy procedures.

SUMMARY OF THE INVENTION

In view of the foregoing, it is an object of the present invention to provide methods and apparatus for orienting a needle guide that overcome drawbacks associated with previously-known methods and apparatus.

It is also an object of the present invention to provide methods and apparatus with improved orientation capabilities, sized to permit use in the surgical field of standard, transperineal brachytherapy procedures.

These and other objects of the present invention are accomplished by providing methods and apparatus for orienting a needle template comprising a template mount that provides for angular repositioning of the needle template with respect to an ultrasound probe. When used in conjunction with previously-known apparatus for longitudinal, horizontal, and vertical orientation of the template, the present invention provides superior control over needle template orientation without increased size, so that brachytherapy needles may be inserted in a manner that avoids skeletal structures. A guide tube is also provided to ensure "straight" insertion of the brachytherapy needles.

Methods of using the present invention are also provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 3A–3E are views of apparatus constructed in accordance with the present invention shown, respectively, in isometric view coupled to a needle template, in isometric view in isolation, in top view, in sectional view along section line A—A of FIG. 3B, and in top view coupled to standard brachytherapy apparatus and illustrating a method of use;

DETAILED DESCRIPTION OF THE INVENTION

The present invention provides methods and apparatus for improved administration of brachytherapy. More particularly, the present invention provides a mount for a needle template that allows the template to pivot with respect to the mount, thereby providing improved orientation capabilities for implantation of radioactive seeds.

Figure 1:
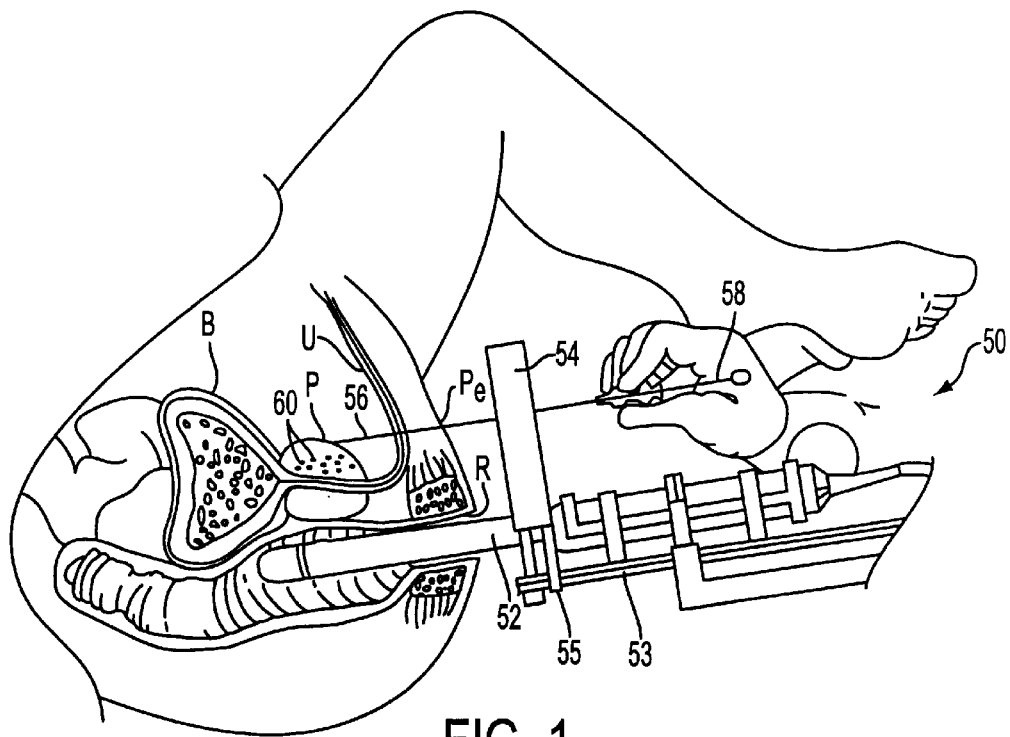
FIG. 1 is a schematic view of a prior art method of performing brachytherapy.

Referring now to FIGS. 1 and 2A–2G, the prior art method of performing brachytherapy is described. The method and apparatus as described here are taught by Peter Grimm, DO, in a pamphlet entitled, *"Ultrasound Guided Implantation of the Prostate: A Practical Review Course."* As seen in FIG. 1, brachytherapy apparatus 50 comprises transrectal ultrasound probe 52, needle template 54, needle 56, plunger 58, and radioactive seeds 60. Ultrasound probe 52 is advanced through a patient's rectum R to facilitate imaging of the patient's prostate P. Prostate P surrounds the urethra U and is just proximal of the bladder B. Needle 56, loaded with seeds 60 and plunger 58, is advanced through needle template 54, through the patient's perineum Pe, and into prostate P, where needle 56 is retracted and seeds 60 are delivered to the patient.

Needle template 54 is attached to template mount 55, which is slidably received on track 53 and may be longitudinally repositioned with respect to ultrasound probe 52. Alternatively, mount 55 may be rigidly attached to track 53, in which case the track may be longitudinally repositioned with respect to ultrasound probe 52.

With reference to FIG. 2, a previously known seed delivery method is described in greater detail. Needle 56 has proximal end 62, sharpened distal end 64, and a lumen extending therebetween. Proximal end 62 comprises hub 66 for easy grasping of the needle. The opening at the distal tip of needle 56 is initially filled with bone wax that melts when placed inside the body. The needle lumen typically is filled in an alternating pattern of seeds 60 and spacers 68.

Figure 2A:
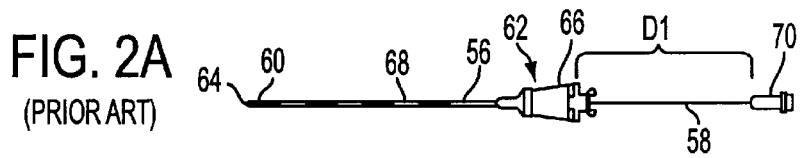
FIGS. 2A–2G are schematic views detailing the prior art method in greater detail.

Once a required number of seeds have been loaded, plunger 58 is inserted into proximal end 62 of needle 56 and is advanced distally until it abuts the proximal-most seed. Plunger 58 comprises grip 70 at its proximal end. The distance from the distal end of grip 70 to the distal end of the plunger is equal to the length of needle 56. Thus, since seeds 60 and spacers 68 are of known length, measurement of D1, the distance plunger 58 extends proximally of needle 56 in the loaded configuration, provides verification of the number of seeds 60 located within the needle lumen, as seen in FIG. 2A.

Figure 2B:
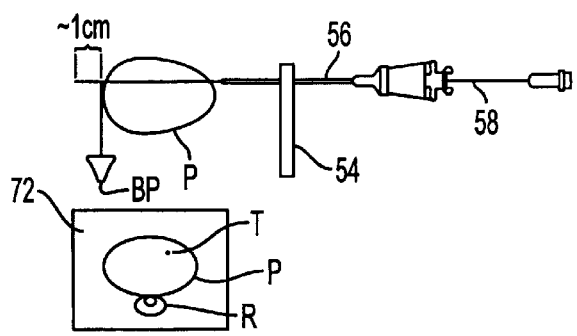
Figure 2C:
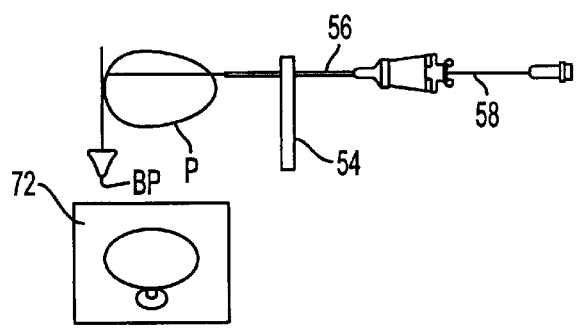
Figure 2D:
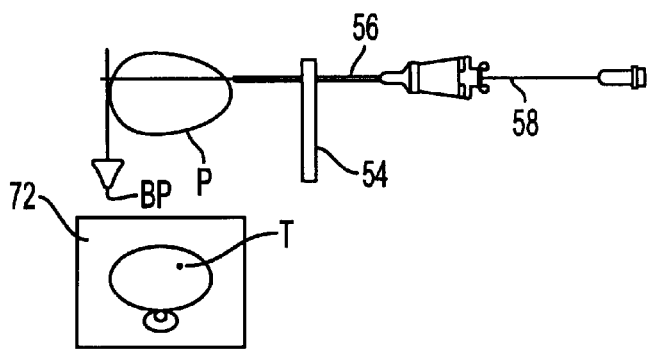

Ultrasound probe 52 provides signals that are converted by a previously known ultrasound system to display ultrasonic image 72 of base plane BP, which is located at a tangent to the distal surface of prostate P. All positions within the prostate are determined relative to base plane BP. With seeds 60 loaded into needle 56 and the distance D1 verified; the needle, seeds, and plunger 58 are inserted through needle template 54 and into the patient until needle 56 appears as target T on ultrasonic image 72 and extends about a centimeter distal of base plane BP, as depicted in FIG. 2B. The apparatus is then retracted until target T disappears (FIG. 2C) and is once again advanced until target T just reappears (FIG. 2D). All the while, distance D1 is maintained.

Figure 2E:
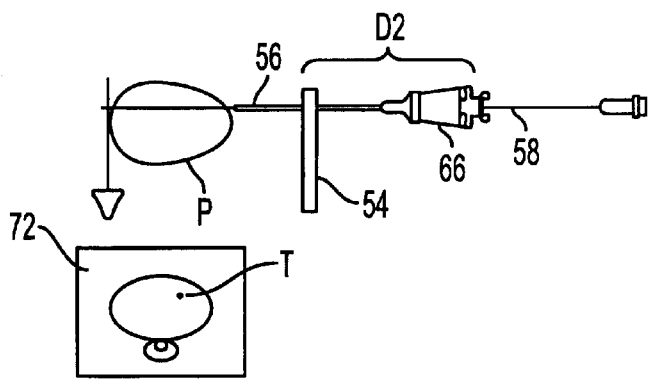
Figure 2F:
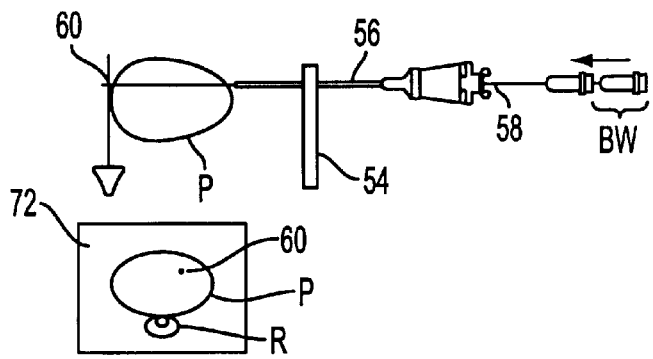

Once needle 56 is aligned with base plane BP, a distance D2 between the proximal face of needle template 54 and the proximal face of hub 66 is established, as shown in FIG. 2E. D2 may be altered via template mount 55 by longitudinally repositioning template 54 relative to ultrasound probe 52. D2 serves as the reference distance for determining insertion depth for all subsequent needle insertions. A first medical practitioner then holds needle 56 stationary while a second medical practitioner advances the first seed 60 to the distal tip of the needle with plunger 58, as depicted in FIG. 2F. The advancement distance equals the length BW of the bone wax used to plug the tip.

Figure 2G:
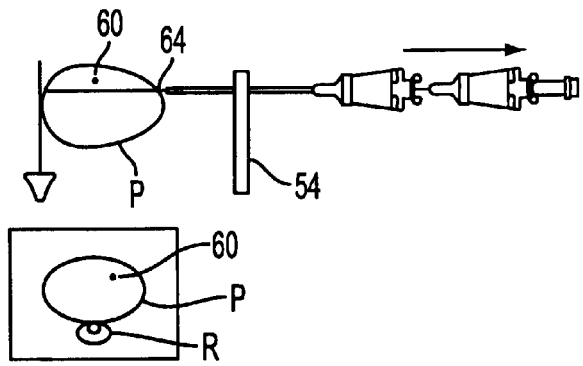

Finally, the second medical practitioner holds plunger 58 stationary while the first practitioner rotates and proximally retracts needle 56 to sew the seeds in a line within prostate P, as shown in FIG. 2G. The needle and plunger are then removed from the patient, and the procedure is repeated at other locations as necessary.

While the previously known apparatus used to position ultrasound probe 52 and needle template 54 may allow longitudinal, vertical, and/or horizontal orientation of needle template 54, the apparatus does not allow angular reorientation of the the template during a brachytherapy procedure. Angular reorientation is expected to beneficially overcome anatomical constraints, such as skeletal structures, that may limit the medical practitioner's ability to deliver radioactive brachytherapy seeds into the prostate in proper alignment.

With reference now to FIGS. 3A–3D, apparatus constructed in accordance with the present invention is described. Apparatus 100 comprises needle template mount 102. Mount 102 illustratively comprises upper half 103 and lower half 104, but it should be understood that mount 102 may alternatively be formed as a single piece. Upper half 103 and lower half 104 combine to form ultrasound bore 106, in which ultrasound probe 52 is slidably received. Lower half 104 further comprises track bores 108, which slidably receive track 53. Upper half 103 further comprises arc slot 110, which provides for angular reorientation of needle template 54 during a brachytherapy procedure. Template 54 comprises stem 112 that is translatably received in slot 110; by translating stem 112 within slot 110, the longitudinal axis of template 54 may be oriented at an angle to the longitudinal axis of ultrasound probe 52. Upper half 103 optionally may still further comprise markings 114, which allow a medical practitioner to determine and set that angle.

Referring now to FIG. 3E, as well as FIGS. 1–3D, a method of using apparatus 100 is described. The dotted lines of FIG. 3E represent angular reorientation of the longitudinal axis of needle template 54 with respect to the longitudinal axis of ultrasound probe 52.

With seeds 60 loaded into needle 56 and the distance D1 verified; the needle, seeds, and plunger 58 are inserted through needle template 54 and into the patient. The longitudinal axis of needle template 54 may initially be aligned with the longitudinal axis of ultrasound probe 52, or it may be oriented at an angle. The distance D2 is established and may be altered by longitudinally repositioning template mount 102, with attached template 54, relative to ultrasound probe 52. As will of course be understood, longitudinal repositioning of template 54 may also require angular repositioning when the template is aligned at an angle, to ensure proper alignment with prostate P.

The first medical practitioner holds needle 56 stationary while the second medical practitioner advances the first seed 60 to the distal tip of the needle with plunger 58. The second medical practitioner then holds plunger 58 stationary while the first practitioner rotates and proximally retracts needle 56 to sew the seeds in a line within prostate P. The needle and plunger are removed from the patient.

The seed delivery procedure is repeated at other locations as necessary. In accordance with the present invention, needle template 54 may be angularly reoriented with respect to ultrasound probe 52 between seed delivery procedures, as seen in FIG. 3E. Angular reorientation may, for example, be used when anatomical constraints, such as skeletal structures, for example, the pelvis and pubic bone, are expected to limit the medical practitioner's ability to deliver radioactive brachytherapy seeds into the prostate in proper alignment. Stem 112 of template 54 translates within arc slot 110 to angularly reorient the template. The medical practitioner optionally may use markings 114 to orient template 54 at a specific angle to ultrasound probe 52. The procedure outlined hereinabove is then repeated as necessary.

Figure 4:
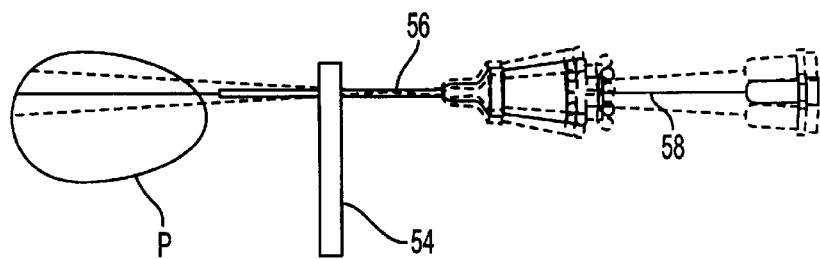
FIG. 4 is a schematic view detailing an additional disadvantage of the prior art method of FIGS. 2A–2G.

Referring now to FIG. 4, an additional shortcoming of the prior art method of brachytherapy delivery is described. If needle 56 is not "straight" when advanced through needle template 54, the needle may be misaligned when advanced into prostate P, as illustrated by dotted lines in FIG. 4. This may lead to improper delivery positioning of brachytherapy seeds, and, thus, potentially harmful improper distribution of radiation exposure within the patient. In the context of the present invention, "straight" advancement comprises advancing a brachytherapy needle through a needle template such that the needle is disposed at substantially no angle with respect to the longitudinal axis of the template.

Figure 5:
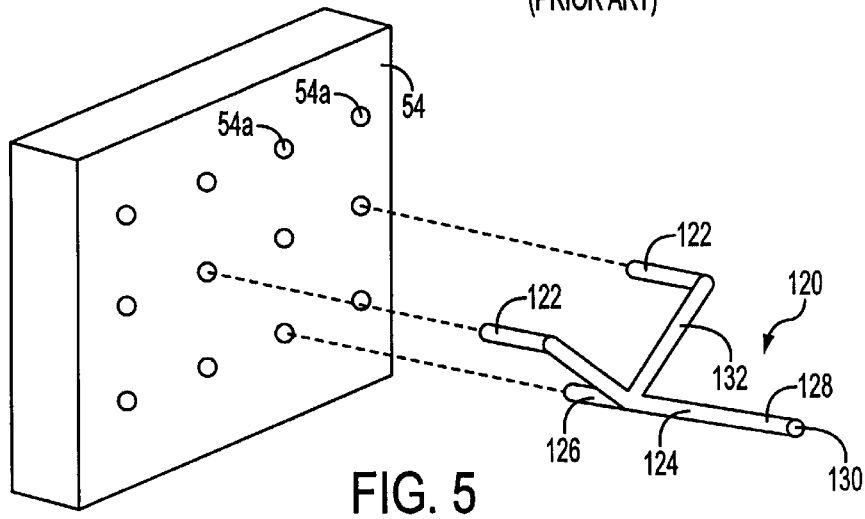
FIG. 5 is an isometric view of guide tube apparatus in accordance with the present invention that addresses the disadvantage of FIG. 4 and ensures "straight" insertion of brachytherapy needles.

With reference to FIG. 5, apparatus in accordance with the present invention is provided that ensures straight advancement of a brachytherapy needle. Guide tube 120 comprises posts 122 configured for insertion within template holes 54a of needle template 54. Guide tube 120 further comprises elongated member 124 having proximal end 126, distal end 128, and lumen 130 extending therebetween. Proximal end 126 is configured for insertion within template holes 54a, and lumen 130 is configured to slidingly receive needle 56. Mount 132 connects posts 122 to elongated member 124.

Guide tube 120 is preferably fabricated from a substantially rigid material to mitigate angular deflection of elongated member 124 with respect to mount 132, and may be disposable or reusable. Guide tube 120 further may comprise measurement indicia, scales, or stops in order to regulate needle insertion depth. Although, in FIG. 5, the guide tube is illustratively provided with two posts 122, it will be apparent to one of skill in the art that guide tube 120 may alternatively be provided with any other number of posts, or no posts.

Figure 6:
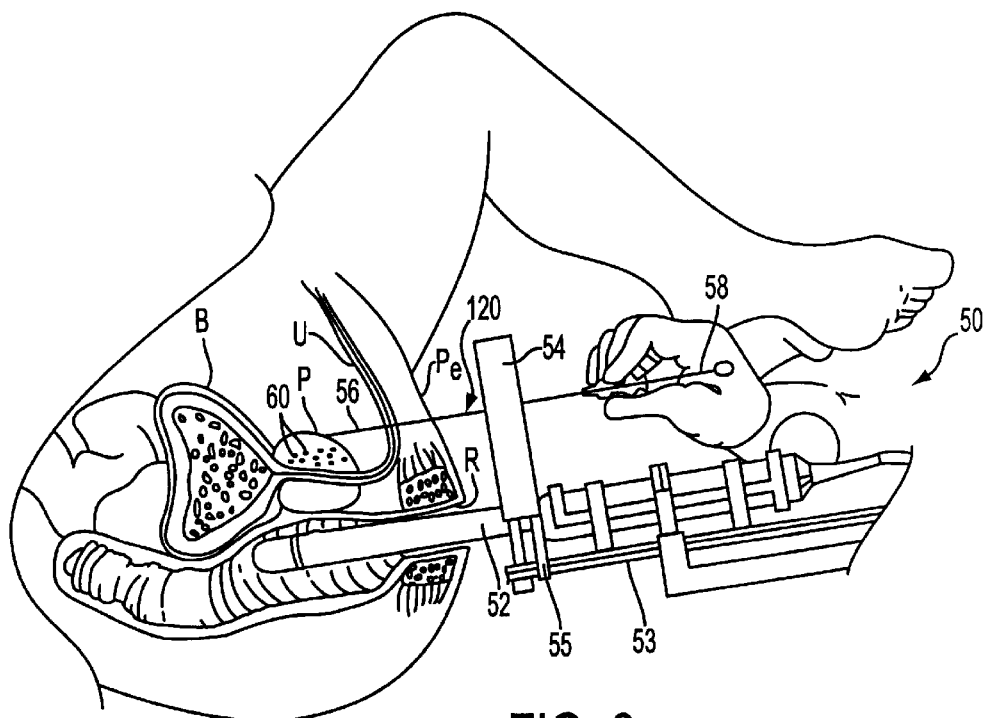
FIG. 6 is a schematic view of a method of performing brachytherapy with the apparatus of FIG. 5.

Referring now to FIG. 6, a method of using guide tube 120 with the apparatus of FIG. 1 is described. As seen in FIG. 6, guide tube 120 is coupled to needle template 54, and needle 56 is advanced through lumen 130 of guide tube 120. The guide tube ensures that needle 56 is advanced straight and is properly positioned within the patient's prostate P. Guide tube 120 may then be repositioned in other template holes 54a, and needle 56 may be reinserted through lumen 130 into the patient at another target location.

As will of course be understood, guide tube 120 may also be used in conjunction with apparatus 100 of FIG. 3. When used in conjunction with apparatus 100, guide tube 120 provides superior control over positioning of needle 56, as compared to current apparatus and methods.

Although preferred illustrative embodiments of the present invention are described hereinabove, it will be evident to one skilled in the art that various changes and modifications may be made without departing from the invention. For example, guide tube 120 may be coupled to the opposite side of needle template 54 such that elongated member 124 extends away from the patient, thereby facilitating rapid repositioning of guide tube 120 in other template holes 54a of needle template 54. It is intended in the appended claims to cover all such changes and modifications that fall within the true spirit and scope of the invention.

What is claimed is:

1. Apparatus for administration of brachytherapy, the apparatus comprising:
   an ultrasound probe having an exterior surface;
   a needle template mount longitudinally positionable along the exterior surface and comprising an arc slot; and
   a needle template translatably received within the arc slot to facilitate angular reorientation of a longitudinal axis of the template with respect to a longitudinal axis of the ultrasound probe.

2. The apparatus of claim 1, wherein the mount further comprises a bore, the exterior surface of the ultrasound probe slidably received within the bore to facilitate longitudinal positioning of the mount along the exterior surface.

3. The apparatus of claim 1 further comprising a track, the mount slidably received on the track to facilitate longitudinal positioning of the mount along the exterior surface.

4. The apparatus of claim 1 further comprising a track, the mount rigidly attached to the track and the track longitudinally positionable with respect to the ultrasound probe to facilitate longitudinal positioning of the mount along the exterior surface.

5. The apparatus of claim 1, wherein the needle template mount further comprises markings disposed about the arc lumen.

6. The apparatus of claim 5, wherein the markings are configured to facilitate angular reorientation of the longitudinal axis of the needle template to a specified angle to the longitudinal axis of the ultrasound probe.

7. The apparatus of claim 1 further comprising a guide tube coupled to the needle template.

8. The apparatus of claim 7, wherein the guide tube comprises an elongated member having proximal and distal ends and a lumen extending therebetween, the lumen disposed parallel to the longitudinal axis of the needle template.

9. The apparatus of claim 8, wherein the guide tube comprises at least one post coupled to the elongated member by a mount.

10. The apparatus of claim 7, wherein the guide tube further comprises means for regulating needle depth insertion.

11. The apparatus of claim 10, wherein the means for regulating needle depth insertion are chosen from the group consisting of measurement indicia, scales, and stops.

12. A method of administering brachytherapy, the method comprising:
  providing apparatus comprising an ultrasound probe, a needle template mount slidably disposed about the ultrasound probe, and a needle template disposed on the mount such that the template may be angularly oriented with respect to the probe;
  longitudinally positioning the mount at a desired location with respect to the probe; and
  angularly orienting the template at a desired angle with respect to the probe.

13. The method of claim 12 further comprising inserting the ultrasound probe through a patient's rectum to facilitate imaging of the patient's prostate and a reference plane.

14. The method of claim 13 further comprising inserting a sharpened distal tip of a needle containing brachytherapy seeds through the template into a target location within the patient's prostate until it is aligned with the reference plane.

15. The method of claim 14 further comprising retracting the needle in a manner that delivers the brachytherapy seeds into the prostate.

16. The method of claim 12, wherein the needle template mount comprises markings.

17. The method of claim 16, wherein angularly orienting the template at a desired angle with respect to the probe comprises using the markings as a guide to ensure that the template is oriented at the desired angle.

18. The method of claim 14 further comprising providing a guide tube coupled to the needle template, wherein inserting the needle through the template comprises inserting the needle through the guide tube.

19. The method of claim 18, wherein the guide tube facilitates straight insertion of the needle into the target location.

20. Apparatus for improved positional control during administration of brachytherapy, the apparatus comprising:
  a needle template mount having an arc slot; and
  a needle template translatably received within the arc slot to facilitate angular reorientation of a longitudinal axis of the template with respect to a longitudinal axis of the mount.

21. The apparatus of claim 20 further comprising an ultrasound probe having an exterior surface, the needle template mount longitudinally positionable along the exterior surface.

22. The apparatus of claim 21, wherein the mount further comprises a bore, the exterior surface of the ultrasound probe slidably received within the bore to facilitate longitudinal positioning of the mount along the exterior surface.

23. The apparatus of claim 21 further comprising a track, the mount slidably received on the track to facilitate longitudinal positioning of the mount along the exterior surface.

24. The apparatus of claim 21 further comprising a track, the mount rigidly attached to the track and the track longitudinally positionable with respect to the ultrasound probe to facilitate longitudinal positioning of the mount along the exterior surface.

25. The apparatus of claim 20, wherein the needle template mount further comprises markings disposed about the arc slot.

26. The apparatus of claim 25, wherein the markings are configured to facilitate angular reorientation of the longitudinal axis of the needle template to a specified angle to the longitudinal axis of the needle template mount.

27. The apparatus of claim 20 further comprising a needle containing brachytherapy seeds, the needle configured to pass through the needle template.

28. The apparatus of claim 20 further comprising a guide tube coupled to the needle template.

29. The apparatus of claim 28, wherein the guide tube comprises an elongated member having proximal and distal ends and a lumen extending therebetween, the lumen disposed parallel to the longitudinal axis of the needle template.

30. The apparatus of claim 7, wherein the guide tube further comprises means for regulating needle depth insertion.

31. Apparatus for improved positional control during administration of brachytherapy treatment, the apparatus comprising:
  a needle template; and
  a guide tube coupled to the needle template.

32. The apparatus of claim 31 further comprising an ultrasound probe having an exterior surface, the needle template longitudinally positionable along the exterior surface.

33. The apparatus of claim 31 further comprising a needle containing brachytherapy seeds, the needle configured to pass through the guide tube.

34. The apparatus of claim 31, wherein the guide tube comprises an elongated member having proximal and distal ends and a lumen extending therebetween, the lumen disposed parallel to the longitudinal axis of the needle template.

35. The apparatus of claim 34, wherein the guide tube comprises at least one post coupled to the elongated member by a mount.

36. The apparatus of claim 31, wherein the guide tube further comprises means for regulating needle depth insertion.

37. The apparatus of claim 32, wherein the means for regulating needle depth insertion are chosen from the group consisting of measurement indicia, scales, and stops.

38. A method of administering brachytherapy to a patient, the method comprising:

providing apparatus comprising an ultrasound probe, a needle template slidably disposed about the ultrasound probe, and a guide tube coupled to the needle template;

longitudinally positioning the mount at a desired location with respect to the probe; and inserting a sharpened distal tip of a needle containing brachytherapy seeds through the guide tube into a target location within the patient.

39. The method of claim 38 further comprising, prior to inserting the needle, inserting the ultrasound probe through the patient's rectum to facilitate imaging of the patient's prostate and a reference plane.

40. The method of claim 39, wherein inserting the needle into the target location comprises inserting the needle into the patient's prostate until it is aligned with the reference plane.

41. The method of claim 40 further comprising retracting the needle in a manner that delivers the brachytherapy seeds into the prostate.

42. The method of claim 38, wherein the guide tube facilitates straight insertion of the needle into the target location.

* * * * *